(12) United States Patent
Weling et al.

(10) Patent No.: US 9,228,956 B2
(45) Date of Patent: Jan. 5, 2016

(54) IN-SITU FLUID ANALYSIS SENSOR BOLT

(71) Applicant: Spectro Scientific, Inc., Chelmsford, MA (US)

(72) Inventors: Aniruddha S. Weling, Framingham, MA (US); Russell S. Girgenti, Sun City Center, FL (US); Matthew B. Fratkin, Brookline, MA (US); Patrick F. Henning, Concord, MA (US)

(73) Assignee: Spectro Scientific, Inc., Chelmsford, MA (US)

( * ) Notice: Subject to any disclaimer, the term of this patent is extended or adjusted under 35 U.S.C. 154(b) by 161 days.

(21) Appl. No.: 14/048,781

(22) Filed: Oct. 8, 2013

(65) Prior Publication Data
US 2015/0097120 A1 Apr. 9, 2015

(51) Int. Cl.
*G01F 23/292* (2006.01)
*G01N 21/85* (2006.01)
*G01N 21/3577* (2014.01)

(52) U.S. Cl.
CPC ........ *G01N 21/8507* (2013.01); *G01N 21/3577* (2013.01); *G01F 23/292* (2013.01); *G01F 23/2925* (2013.01); *G01N 2021/8521* (2013.01); *Y10T 29/49117* (2015.01)

(58) Field of Classification Search
CPC .............. G01F 23/292; G01F 23/2925; G01N 21/8507
See application file for complete search history.

(56) References Cited

U.S. PATENT DOCUMENTS

| | | | |
|---|---|---|---|
| 5,170,056 A | 12/1992 | Berard et al. | |
| 6,333,512 B1 * | 12/2001 | Wirthlin | 250/577 |
| 8,213,006 B2 | 7/2012 | Myrick et al. | |

* cited by examiner

*Primary Examiner* — David Porta
*Assistant Examiner* — Hugh H Maupin
(74) *Attorney, Agent, or Firm* — Iandiorio Teska & Coleman, LLP

(57) ABSTRACT

A sensor and associated methods wherein a bolt or rod stem includes a flow path through and across the stem. A source of radiation within the stem is configured to direct radiation through the flow path and a detector subsystem in the stem is configured to detect radiation passing through the flow path. A head includes electrical conductors for the radiation source and detector subsystem resulting in a compact, inexpensive sensor.

28 Claims, 6 Drawing Sheets

IN-SITU FLUID ANALYSIS SENSOR BOLT

GOVERNMENT RIGHTS

This invention was partially developed under U.S. Army SBIR Contract #W911 W6-06-0007-0002 "Integrated On-Line Monitor for HUMS". The Government may have certain rights in the invention.

FIELD OF THE INVENTION

The subject invention relates, in one particular example, to infrared spectroscopy.

BACKGROUND OF THE INVENTION

Fluid used in machinery and the like (engines, compressors, hydraulic devices) can be monitored by infrared spectroscopy using known systems. In many cases, fluid is withdrawn from the machine and sent to a laboratory to determine the percentages of water, fuel, antifreeze, or the like in the fluid as a measure of machine health.

For in-situ systems, the fluid must be interrogated optically with at least the return radiation directed in some fashion to the infrared spectrometer. Generally, doing so involves using a waveguide (such as a fiber optic) to gather the radiation from the analysis cell, which resides within the fluid stream. See, for example, U.S. Pat. No. 5,170,056 incorporated herein by this reference. The analysis cell itself typically consists of either an attenuated total reflectance (ATR) element or a mirror coupled to the end of a fiber optic probe. Many such infrared spectroscopy systems for in-situ monitoring are complex and expensive. In place of a spectrometer-based system are systems such as in U.S. Pat. No. 8,213,006 (incorporated herein by this reference) where specific features of the fluid are desired and a filter or plurality of specially designed filters may be used to monitor such features. Such approaches may significantly decrease costs and increase optical throughput in systems where an entire infrared spectrum is not needed.

SUMMARY OF THE INVENTION

In one aspect, a compact infrared analyzer which can be screwed into a fluid bulkhead (e.g., gearbox, oil pan, or the like) is provided. Such an analyzer is designed to overcome issues associated with providing a sufficient and reproducible sampling path length of fluid as can be encountered with, for example, ATR cells. At the same time, it provides a passive, monolithic design which urges fluid into the key sampling path length.

Featured is a sensor comprising a bolt stem with a flow path through and across the stem. A source of radiation within the stem is configured to direct radiation through the flow path and a detector subsystem in the stem is configured to detect radiation passing through the flow path. A bolt head includes electrical conductors for the radiation source and detector subsystem.

In one example, the stem includes a threaded portion proximate the head. The flow path may include three spaced openings through a wall of the bolt stem. In one version, the bolt stem defines a first chamber on one side of the flow path including the source of radiation and a second chamber on an opposite side of the flow path including the detector subsystem. The first chamber can be sealed by a first window adjacent the flow path and the second chamber can be sealed by a second window adjacent the flow path. In one embodiment, the windows are zinc selenide windows. In another version, the sensor stem includes spaced prongs defining a flow path therebetween. The spaced prongs preferably define a narrower sampling gap with spaced windows on each side thereof. Further included may be optical elements positioned to direct infrared radiation from the source, through the windows, across the gap, and to the detector subsystem.

The infrared source is preferably a broadband infrared source with a parabolic reflector reflecting collimated radiation towards the flow path. Also, the detector subsystem preferably includes a plurality of infrared detectors such as thermopile or thermocouple devices with a tailored filter for each detector. Thus, the detector subsystem may be used to provide multiple fluid properties from a single sensor.

The bolt head may include a connector including pins for the electrical conductors. Further included may be an asset identification subsystem configured to provide an asset identifying signal to at least one said electrical conductor. In one example the asset identifying subsystem includes a memory. The detector subsystem may also include an electronic assembly in the stem.

Also featured is a sensor comprising a stem immersible in a fluid and including a gap defining a flow path, a source of radiation configured to direct radiation across the gap, and a detector subsystem configured to detect radiation passing through the gap. A head exterior to the fluid includes a connector with electrical conductors extending to the source and the detector subsystem.

In one example, the stem includes a first chamber within a stem wall on one side of the gap housing the source of radiation and a second chamber within the stem wall on an opposite side of the gap housing the detector subsystem. The flow path may include a plurality of circumferentially spaced openings through the stem wall.

An in-situ sensing method in accordance with the invention includes immersing a stem with a source of radiation and a detector subsystem therein within fluid behind a bulkhead, allowing fluid between the source of radiation and the detection subsystem, energizing the source of radiation, and processing signals output by the detector subsystem via a connector associated with a head outside the bulkhead.

Also featured is a sensing method comprising fabricating a bolt stem to include a flow path through and across the stem, disposing a source of radiation within the stem oriented to direct radiation through the flow path, positioning a detector subsystem in the stem to detect radiation from the source of radiation passing through the flow path, and processing signals from the detector subsystem.

Further featured is a method of manufacturing a sensor wherein a stem is partitioned to include a gap defining a flow path. A source of radiation is included within the stem to direct radiation across the gap. A detector subsystem within the stem detects radiation passing through the gap. There are conductors for energizing the source of radiation and processing signals from the detector subsystem.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
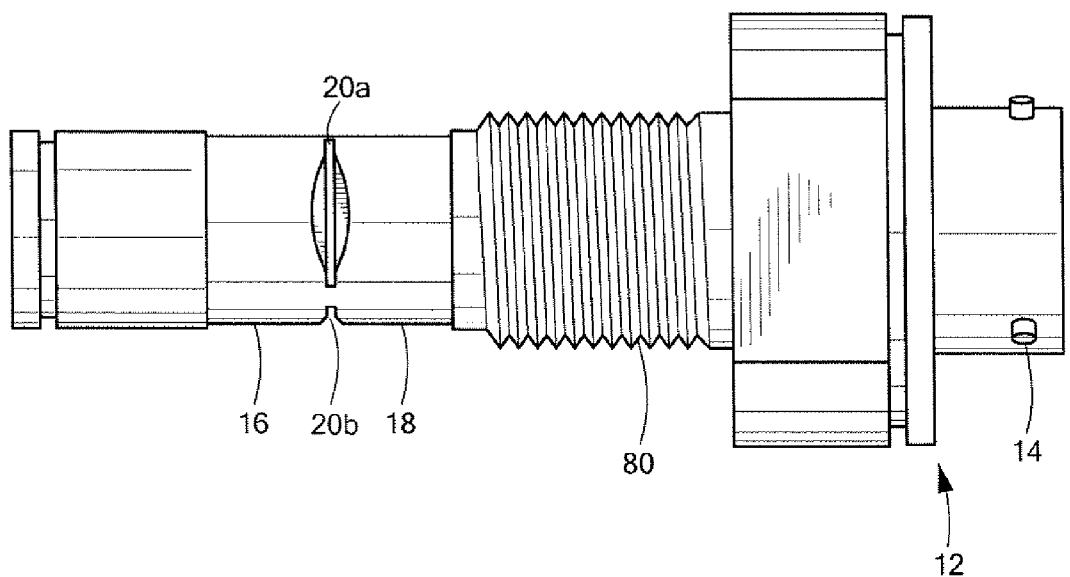
FIG. 1 is a schematic three dimensional view showing an example of a sensor in accordance with the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 depicts a rod like sensor 10, in one example, with bolt head 12 including an electrical connector 14 (e.g., a box mount 12-pin connector) and bolt stem 16 with three spaced chamfered elongate openings through the stem outer wall 18. Two openings in the outer wall are shown at 20a and 20b. The openings are preferably circumferentially spaced around the wall and define a flow path for the oil in a gap as discussed below. Stem 16 houses, inter alia, an infrared source on one side of the gap and a detector subsystem on the other side of the gap. The sensor bolt may include a threaded portion 80 proximate head 12.

Figure 2:
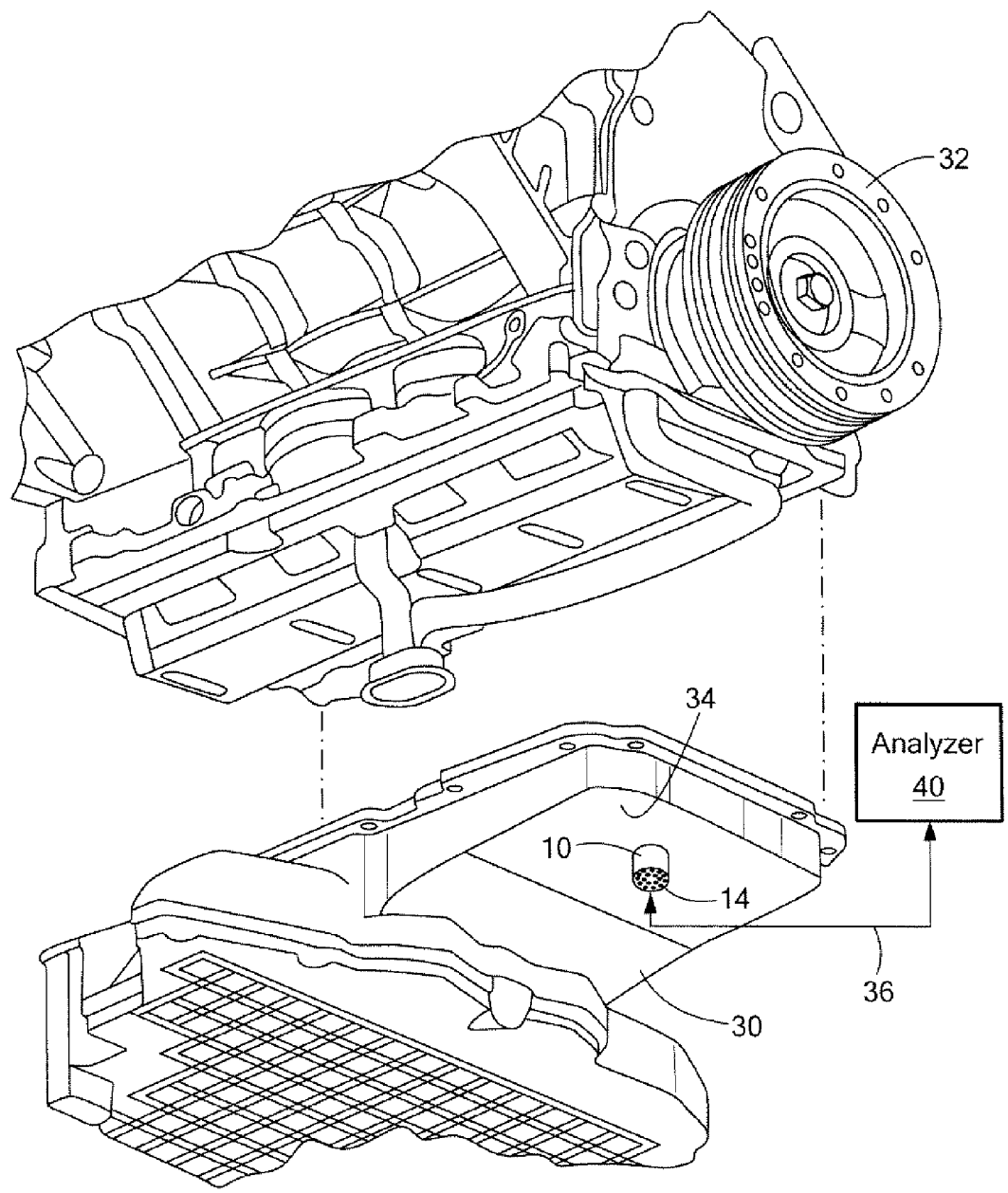
FIG. 2 is a schematic exploded view showing the sensor of FIG. 1 inserted into the oil pan of a machine.

In FIG. 2, sensor bolt 10 has been inserted into oil pan 30 of machine 32, (e.g., an internal combustion engine) such that the bolt stem is immersed in the oil carried by pan 30 and bolt head connector 14 is exterior to the pan bulkhead wall 34. A cable 36 can be used to electrically connect sensor bolt 10 to analyzer 40.

Figure 3:
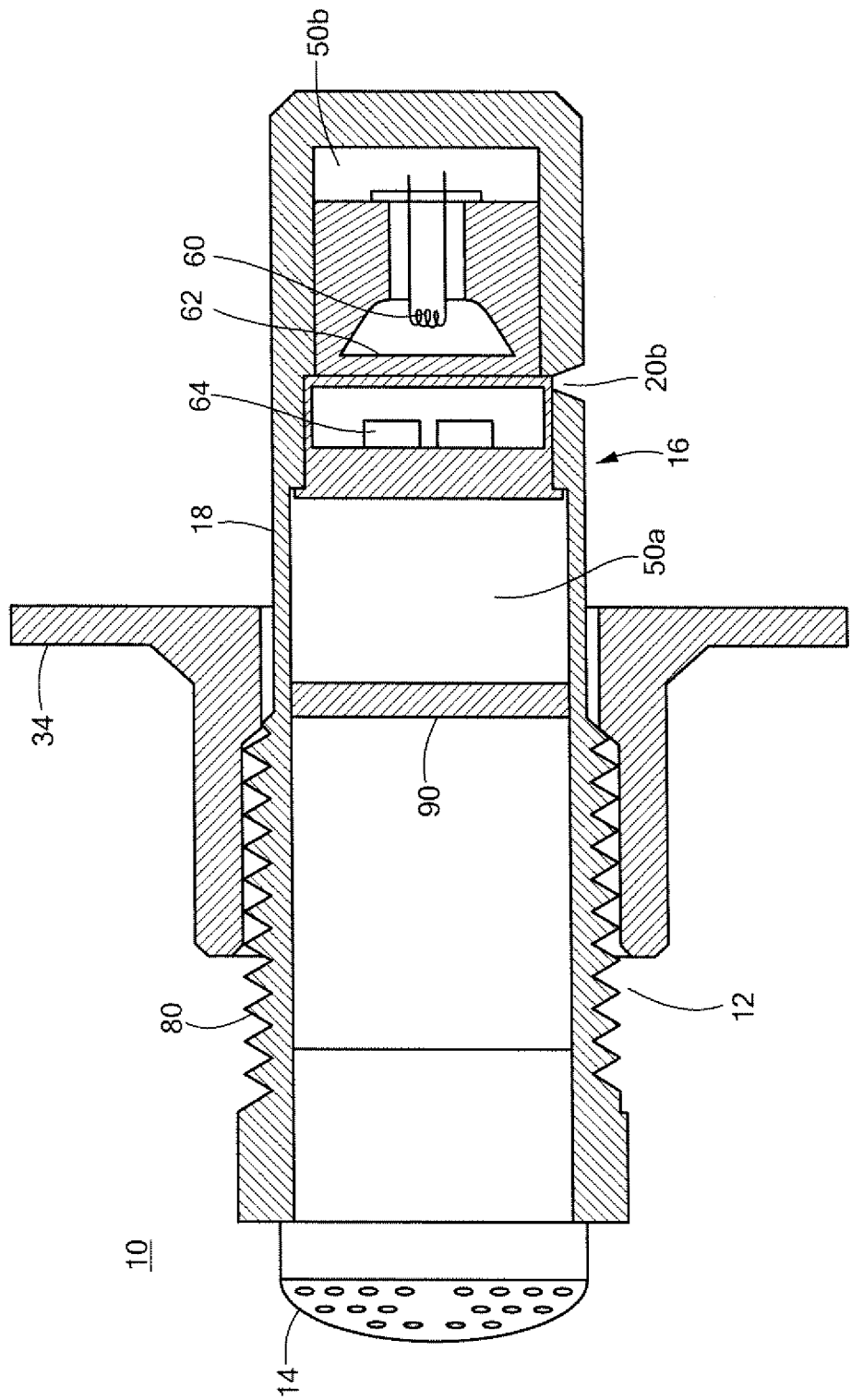
FIG. 3 is a schematic cross-sectional view showing the primary components associated with the sensor or FIG. 1.
Figure 4:
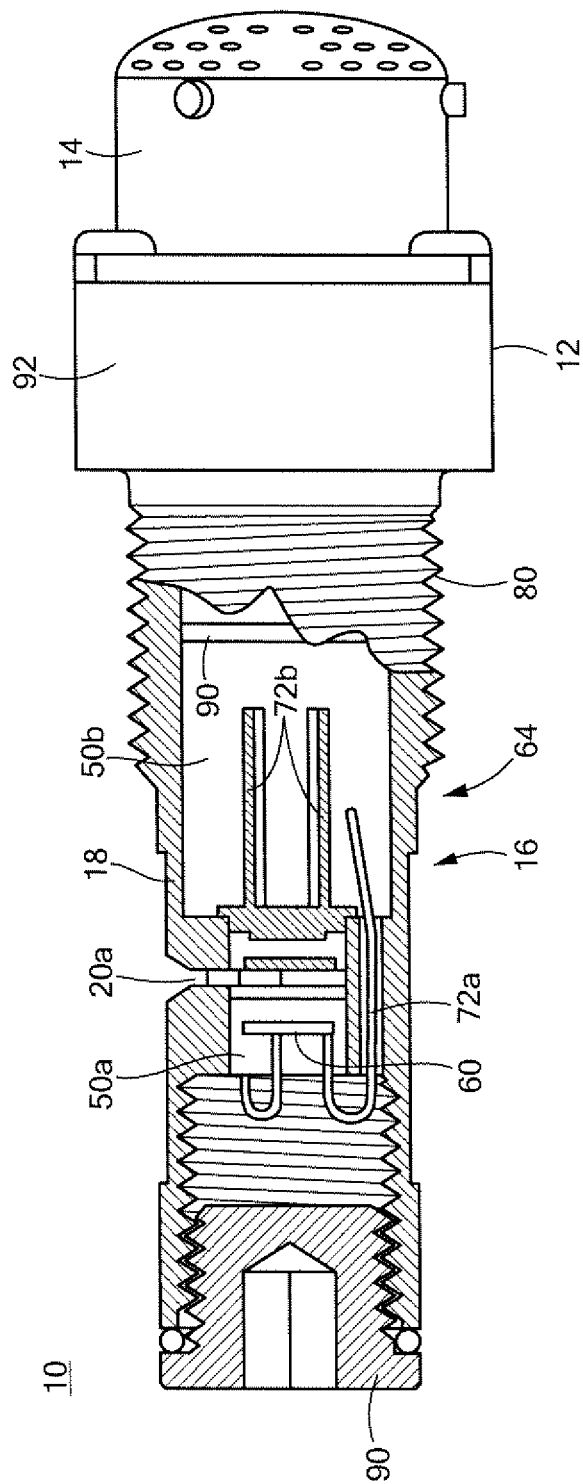
FIG. 4 is a schematic partial cross-sectional view showing another embodiment of a sensor in accordance with the invention.
Figure 6:
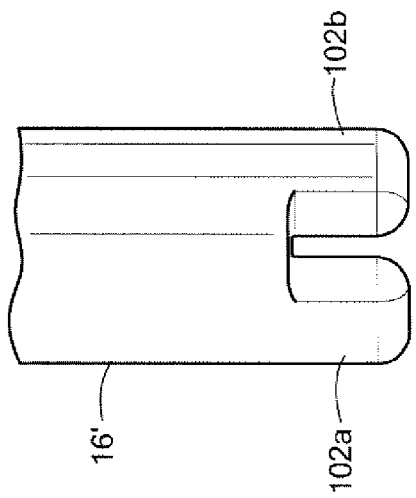
FIG. 6 is a schematic view showing the distal stem end of the sensor of FIG. 5.
Figure 7:
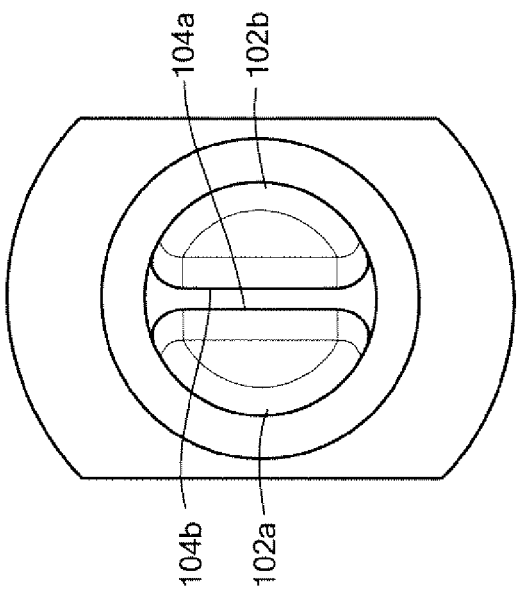
FIG. 7 is an end view of the distal stem end of the sensor of FIG. 5.
Figure 5:
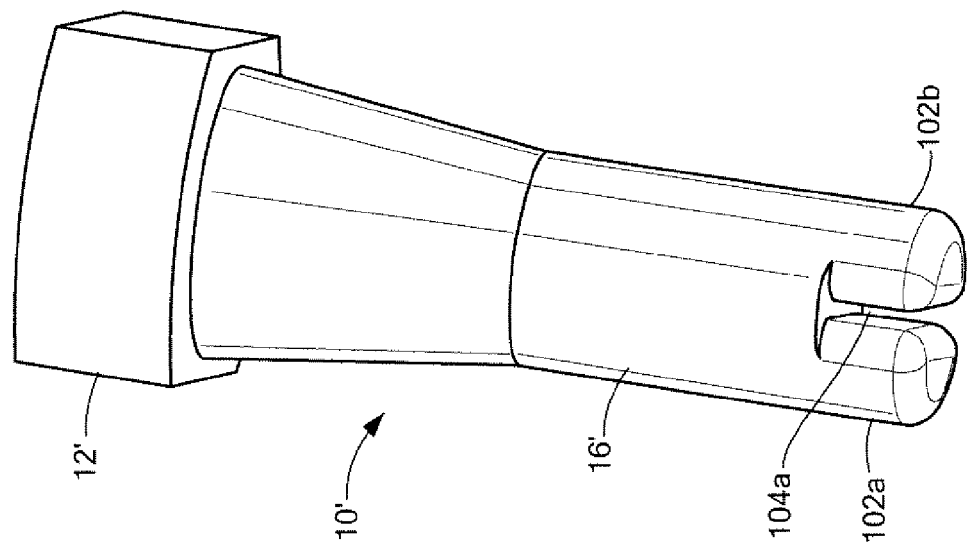
FIG. 5 is a schematic three dimensional view showing another embodiment of a sensor in accordance with an example of the invention.

Bolt stem 16, FIGS. 3-4 thus provides a fluid (e.g., oil) flow path through and across the stem by virtue of one or more openings 20a, 20b, and the like defining a gap between interior sections of the stem. The interior of bolt stem 16 in this particular example is divided or partitioned into two sealed chambers 50a and 50b on opposite sides of the flow path gap. Each chamber is sealed via a stem outer wall 18 and a zinc selenide, quartz, or sapphire window adjacent the flow path gap. Behind one window in chamber 50a is broadband infrared source 60 (e.g., a filament) optionally also provided with a band pass filter, sapphire lens, and/or parabolic reflector 62, FIG. 3 for directing radiation through the gap defining the flow path to detector subsystem 64 in chamber 50b on an opposite side of the flow path. Another window seals chamber 50b with respect to the gap.

Electrical conductor(s) such as at 72a electrically interconnect infrared source 60 to connector 14 and electrical conductors as shown as 72b electrically interconnect detector subsystem 64 with connector 14. Other electrical conductors are possible.

Analyzer 40, FIG. 2 can be configured to energize the infrared source and to process signals output by the detector subsystem. In one example, both the source and the detectors are housed in TO style (e.g., TO-5) electronic packages with leads connected to conductors 72 and the like which lead to the head connector.

The detector subsystem may include four thermopile detectors each including custom infrared filters designed for the specific infrared sensing application. The filters may be multi-layered dielectric thin film coatings on sapphire/silicon substrates which are glued in place one in front of each of the 4 individual detectors. The result, in one embodiment, is an un-cooled four-channel broadband detector configured to analyze wavelengths from 1 to 1,000 microns in a single device to, for example, detect the presence of water and antifreeze in motor oil. The thermocouples themselves may be coated with an ultra-broadband metallic black coating absorber material, or alternatively may be coated with absorbing material which is most sensitive in the wavelength region of interest for that particular detector/filter combination. One of the 4 detectors may be used for system reference and drift compensation. As such it may gather a relatively broadband of infrared radiation. The other 3 detectors may then be "zeroed" off this reference detector.

An electronic circuit board or other assembly 90 can be included in chamber 50b for circuitry and/or electronic chip sets for signal amplification and/or digitization.

Also, an electronic asset identification system can be included to report an identifying signal via the electrical conductors (e.g., pins) of connector 14 and cable 36, FIG. 2 to analyzer 40. An algorithmic approach allows sampling to be uniquely identified by an asset thus tying the science/chemistry directly to the asset. This software algorithm is associated with the asset. The analyzer may include a unique library which allows classification by application rather than the chemistry of the oil.

In this way, a certain model or version of the sensor bolt may be specifically configured to analyze engine oil for a particular type of engine. The sensor bolt reports its configuration to the analyzer which then applies the applicable algorithms for that type of engine end oil. These algorithms are designed to calculate a set of fluid-specific properties. A sensor bolt specifically tailored for hydraulic fluid for a specific hydraulic machine would report its configuration to the analyzer which would then run a different set of algorithms for that asset/machine and report the fluid properties water, oxidation, and incorrect fluid, for example. In this way, the analyzer automatically knows which algorithms to run in order to correctly report parts per million water, percentage soot, and the like. Various technologies can be associated with circuit board 90 to output an identifying signal including a memory chip (e.g., a RAM chip) containing identifying information which is polled by the analyzer, and simple microprocessor such as a 16-bit 8051-based system which is running a real-time operating system. The microprocessor reads the memory chip state and processes the signals emerging from the detectors according to this state. In general the processing is done with a unique algorithm set for each type of fluid analyzed. The chip will point to the correct algorithm, which are stored in processor memory. Such a system serves as the core of the analyzer.

The result is an inexpensive and less complex on-line sensor that employs non-dispersive infrared (NDIR) technology to provide quantitatively accurate fluid analysis results. The rugged immersions sensor package allows for "crevice" sampling of the fluid without the need for extraneous optical components to define or maintain the sample interaction length. The bolt form factor provides infrared sensing technology in a smaller, more rugged and lower cost package that can be easily installed and uninstalled from standard access ports. In some examples, the device is designed to detect fuel leaks, water, and glycol. The ultra-wide bandwidth detection subsystem from approximately 1-1000 microns in wavelength is accomplished in a single device. The steel rod or bolt may include ½ inch NPT mechanical interface that can be used as screw on and screw off for the sensor at an appropriate port where it is fully immersed in the fluid analyte. The bolt can be five inches long or less. The dimensions of the sampling gap can be based on sensitivity requirements and fluid flow parameters. In one example, the gap is 0.004" wide. As shown in FIG. 4, stem 16 terminates in housing 90 which can be removed from the stem in order to insert infrared source 60. Screw button head cap 92 is also included.

Figure 8:
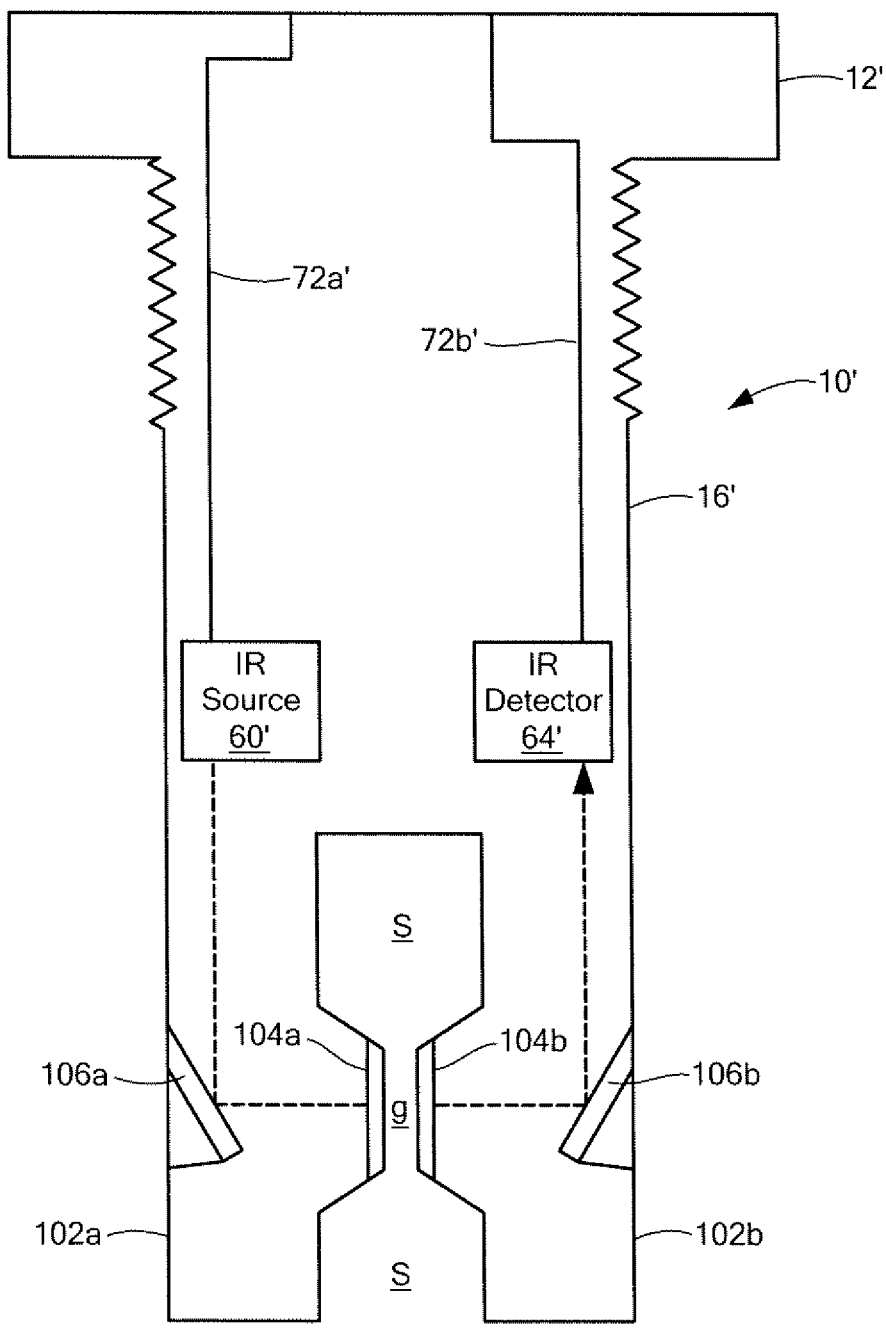
FIG. 8 is a schematic cross-sectional view showing several of the primary components associated with the sensor configured in accordance with the design of FIG. 5.

The infrared radiation must typically be driven through only a small width gap which may inhibit oil flow therethrough. In order to eliminate the need to prewet the sensor, sensor 10', FIGS. 5-8, in another embodiment, includes stem 16' extending from head 12' with spaced distal prongs 102a and 102b defining a flow path therebetween. Windows 104a and 104b protrude into this flow path to provide the requisite small width and here small area sampling gap (e.g., 0.004" wide) but the wide area flow path elsewhere is much larger and wider as shown in FIG. 8 to allow fluid from different directions to easily flow within the flow path and be directed within the gap.

Here, the IR source directs infrared radiation through window 104a via optic(s) including, for example, mirror 106a, through the oil in the sampling gap g, through window 104b, and to detector 64' via optics including, for example, mirror 106b. The gap between the windows may only be 0.004" wide but the interior spacing between the prongs elsewhere in the flow path is much larger (e.g., 0.25") to promote fluid to flow into the spacing between the prongs and into the sampling gap g.

Thus, although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A sensor comprising:
   a bolt stem including:
      a flow path through and across the stem defining a gap between interior sections of the stem,
      a source of radiation within the stem configured to direct radiation through the flow path, and
      a detector subsystem in the stem configured to detect radiation passing through the flow path; and
   a bolt head including electrical conductors for the radiation source and detector subsystem.

2. The sensor of claim 1 in which the stem includes a threaded portion proximate the head.

3. The sensor of claim 1 in which the flow path includes at least three spaced openings through a wall of the bolt stem.

4. The sensor of claim 1 in which the bolt stem defines a first chamber on one side of the flow path including the source of radiation and a second chamber on an opposite side of the flow path including the detector subsystem.

5. The sensor of claim 4 in which the first chamber is sealed by a first window adjacent the flow path and the second chamber is sealed by a second window adjacent the flow path.

6. The sensor of claim 5 in which said windows are zinc selenide windows.

7. The sensor of claim 1 in which the stem includes spaced prongs defining a flow path therebetween.

8. The sensor of claim 7 in which the spaced prongs define a narrower gap with spaced windows on each side thereof.

9. The sensor of claim 8 further including optical elements positioned to direct infrared radiation from the source through the windows, across the gap, and to the detector subsystem.

10. The sensor of claim 1 in which the infrared source is a broadband infrared source.

11. The sensor of claim 10 further including a parabolic reflector for the infrared source reflecting radiation towards the flow path.

12. The sensor of claim 10 in which the detector subsystem includes a plurality of broadband infrared detectors.

13. The sensor of claim 12 in which said detectors are thermopile or thermocouple devices.

14. The sensor of claim 12 further including a filter for each detector.

15. The sensor of claim 1 in which said bolt head includes a connector including pins for the electrical conductors.

16. The sensor of claim 1 further including an asset identification subsystem configured to provide an asset identifying signal to at least one said electrical conductor.

17. The sensor of claim 16 in which the asset identifying subsystem includes a RAM memory module pre-programmed with specific asset-identifying information, including asset and fluid type.

18. The sensor of claim 1 in which the detector subsystem includes an electronic assembly in the stem.

19. A sensor comprising:
   a stem immersible in a fluid and including:
      a gap between interior sections of the stem defining a flow path,
      a source of radiation configured to direct radiation across the gap, and
      a detector subsystem configured to detect radiation passing through the gap; and
   a head exterior to the fluid and including:
      a connector with electrical conductors extending to the source and the detector subsystem.

20. The sensor of claim 19 in which the stem includes a first chamber within a stem wall on one side of the gap housing said source of radiation and a second chamber within the stem wall on an opposite side of the gap housing the detector subsystem.

21. The sensor of claim 20 in which the flow path includes a plurality of circumferentially spaced openings through the stem wall.

22. The sensor of claim 19 in which the stem includes spaced prongs defining a flow path therebetween.

23. The sensor of claim 22 in which the spaced prongs define a narrower gap with spaced windows on each side thereof.

24. The sensor of claim 23 further including optical elements positioned to direct infrared radiation from the source through the windows, across the gap, and to the detector subsystem.

25. An in-situ sensing method comprising:
immersing a stem with a source of radiation and a detector subsystem therein within fluid behind a bulkhead;
allowing fluid to flow through and across the stem to define a gap between interior sections of the stem;
energizing the source of radiation; and
processing signals output by the detector subsystem via a connector associated with a head outside the bulkhead.

26. A sensing method comprising:
fabricating a bolt stem to include a flow path gap between interior sections of the stem and through and across the stem;
disposing a source of radiation within the stem oriented to direct radiation through the flow path;
positioning a detector subsystem in the stem to detect radiation from the source of radiation passing through the flow path; and
processing signals from the detector subsystem.

27. A method of manufacturing a sensor, the method comprising:
partitioning a stem to include flow path with a gap between interior sections of the stem;
including a source of radiation within the stem on one side of the gap to direct radiation across the gap;
including a detector subsystem within the stem on an opposite side of the gap to detect radiation passing through the gap; and
providing conductors for energizing the source of radiation and for processing signals from the detector subsystem.

28. The method of claim 27 in which the source of radiation and detection subsystems are housed in TO packages including leads connected to the conductors.

\* \* \* \* \*